(12) United States Patent
Franks et al.

(10) Patent No.: US 7,722,623 B2
(45) Date of Patent: May 25, 2010

(54) INSTRUMENTS AND METHODS FOR DELIVERING MULTIPLE IMPLANTS

(75) Inventors: Richard W. Franks, Memphis, TN (US); Harold S. Taylor, Memphis, TN (US); Rolando Puno, Prospect, KY (US); Mitch Campbell, Georgetown, IN (US); Luis F. Aguirre, Brighton, TN (US)

(73) Assignee: Warsaw Orthopedic, Inc.

( * ) Notice: Subject to any disclaimer, the term of this patent is extended or adjusted under 35 U.S.C. 154(b) by 754 days.

(21) Appl. No.: 11/433,010

(22) Filed: May 12, 2006

(65) Prior Publication Data

US 2007/0276403 A1 Nov. 29, 2007

(51) Int. Cl.
*A61B 17/58* (2006.01)
(52) U.S. Cl. ...................................... 606/104
(58) Field of Classification Search ............... 606/104, 606/99; A61B 17/58
See application file for complete search history.

(56) References Cited

U.S. PATENT DOCUMENTS

| | | | |
|---|---|---|---|
| 1,537,929 A | 5/1925 | Henry | |
| 2,247,500 A | 7/1941 | Hutchison | |
| 4,811,647 A | 3/1989 | Lindamood | |
| 4,958,873 A | 9/1990 | Akagawa | |
| 4,963,144 A * | 10/1990 | Huene | 606/916 |
| 5,352,231 A | 10/1994 | Brumfield et al. | |
| 5,437,211 A * | 8/1995 | Wolfe | 76/114 |
| 5,445,641 A | 8/1995 | Frigg et al. | |
| 5,590,574 A | 1/1997 | Lide | |
| 5,649,931 A * | 7/1997 | Bryant et al. | 606/104 |
| 5,735,854 A | 4/1998 | Caron et al. | |
| 5,791,207 A | 8/1998 | Ahdoot | |
| 5,941,885 A | 8/1999 | Jackson | |
| 6,112,944 A | 9/2000 | Van Hoorn et al. | |
| 6,129,730 A * | 10/2000 | Bono et al. | 606/291 |
| 6,132,435 A | 10/2000 | Young | |
| 6,224,596 B1 | 5/2001 | Jackson | |
| 6,273,893 B1 | 8/2001 | McAllen, III et al. | |
| 6,283,973 B1 * | 9/2001 | Hubbard et al. | 606/104 |
| 6,328,746 B1 | 12/2001 | Gambale | |
| 6,634,261 B1 | 10/2003 | Griffin | |
| 6,974,466 B2 | 12/2005 | Ahmed et al. | |
| 7,147,641 B2 | 12/2006 | Chen | |
| 7,240,588 B1 * | 7/2007 | Rinner | 76/119 |
| 7,451,893 B2 | 11/2008 | Martin | |
| 2002/0099386 A1 * | 7/2002 | Beger et al. | 606/104 |
| 2002/0193807 A1 * | 12/2002 | Chen | 606/129 |
| 2004/0243139 A1 * | 12/2004 | Lewis et al. | 606/104 |

(Continued)

FOREIGN PATENT DOCUMENTS

DE 298 16 215 U1 11/1998

(Continued)

*Primary Examiner*—Eduardo C Robert
*Assistant Examiner*—Elana B Fisher (57) ABSTRACT

Instruments and methods are provided for delivering multiple implants to multiple implant locations in a patient without requiring a second implant to be loaded onto or engaged to the delivery instrument after delivery of a first implant. The implants can be sequentially engaged using the delivery instrument to the patient or to receptacles of one or more receiving members secured to the patient.

18 Claims, 4 Drawing Sheets

U.S. PATENT DOCUMENTS

| | | |
|---|---|---|
| 2005/0149031 A1 | 7/2005 | Ciccone et al. |
| 2005/0203530 A1 | 9/2005 | Oribe et al. |
| 2005/0222575 A1* | 10/2005 | Ciccone et al. ............ 606/104 |
| 2006/0027592 A1 | 2/2006 | Flamingo et al. |
| 2007/0088363 A1 | 4/2007 | Rezach |
| 2008/0255576 A1 | 10/2008 | Protopsaltis |

FOREIGN PATENT DOCUMENTS

| | | |
|---|---|---|
| FR | 668 187 | 10/1929 |
| GB | 2 355 505 A | 4/2001 |

* cited by examiner

INSTRUMENTS AND METHODS FOR DELIVERING MULTIPLE IMPLANTS

BACKGROUND

Various types of devices and systems have been used for positioning implants into a patient in surgical procedures. Spinal stabilization systems have employed plating systems, rods, anchors, fusions devices, artificial discs, and other implants along or in the spinal column for rigid, dynamic, and semi-rigid spinal stabilization procedures. Such systems often include multiple implant members that must be engaged for the system to be properly installed. There remains a need for instruments and methods for delivering multiple implants to the implantation location while minimizing the time and complexity associated with handling and securing such implants during surgery.

SUMMARY

Instruments and methods for positioning multiple implants in surgical procedures include an instrument for delivering multiple implants configured to permit sequential securement of the implants in multiple receptacles of one or more receiving members or at multiple locations in the patient. The delivery instruments and methods permit implantation of multiple implants without any requirement for re-loading or re-engaging a second implant to the instrument after delivery of a first implant.

In one form, a delivery instrument includes multiple implants axially received along a drive shaft. The implants are sequentially threaded through a threaded distal end bore of the instrument for delivery to the implantation location.

In another form, a delivery instrument includes multiple externally threaded set screws axially positioned along a drive shaft between the drive shaft and an outer housing member. The drive shaft is rotatable relative to the housing to threadingly advance the distal-most set screw through a threaded bore adjacent a distal end opening of the housing member.

In yet another form, a system includes at least one receiving member having at least one receptacle, a delivery instrument positionable adjacent the at least one receptacle, and a plurality of implants carried by the delivery instrument for sequential engagement with multiple ones of the receptacles.

In a further form, a surgical method includes engaging at least one receiving member to a bony structure in a patient; positioning a distal end of a delivery instrument adjacent a first receptacle in the at least one receiving member; threadingly advancing a first implant through an internally threaded bore of the delivery instrument and into the first receptacle while simultaneously advancing a second implant into the threaded bore of the delivery instrument; positioning the distal end of the delivery instrument adjacent a second receptacle of the at least one receiving member; and threadingly advancing the second implant through the internally threaded bore of the delivery instrument and into the second receptacle.

Related features, aspects, embodiments, objects and advantages of the present invention will be apparent from the following description.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Positioning of multiple implants during a surgical procedure is facilitated by a delivery instrument that includes a drive shaft with multiple implants positioned axially therealong. The drive shaft can be manipulated to sequentially deliver the implants to respective implantation locations within the patient during the surgical procedure without a requirement to withdraw the instrument and load or engage a second implant to the delivery instrument after delivery of a first implant.

Figure 1:
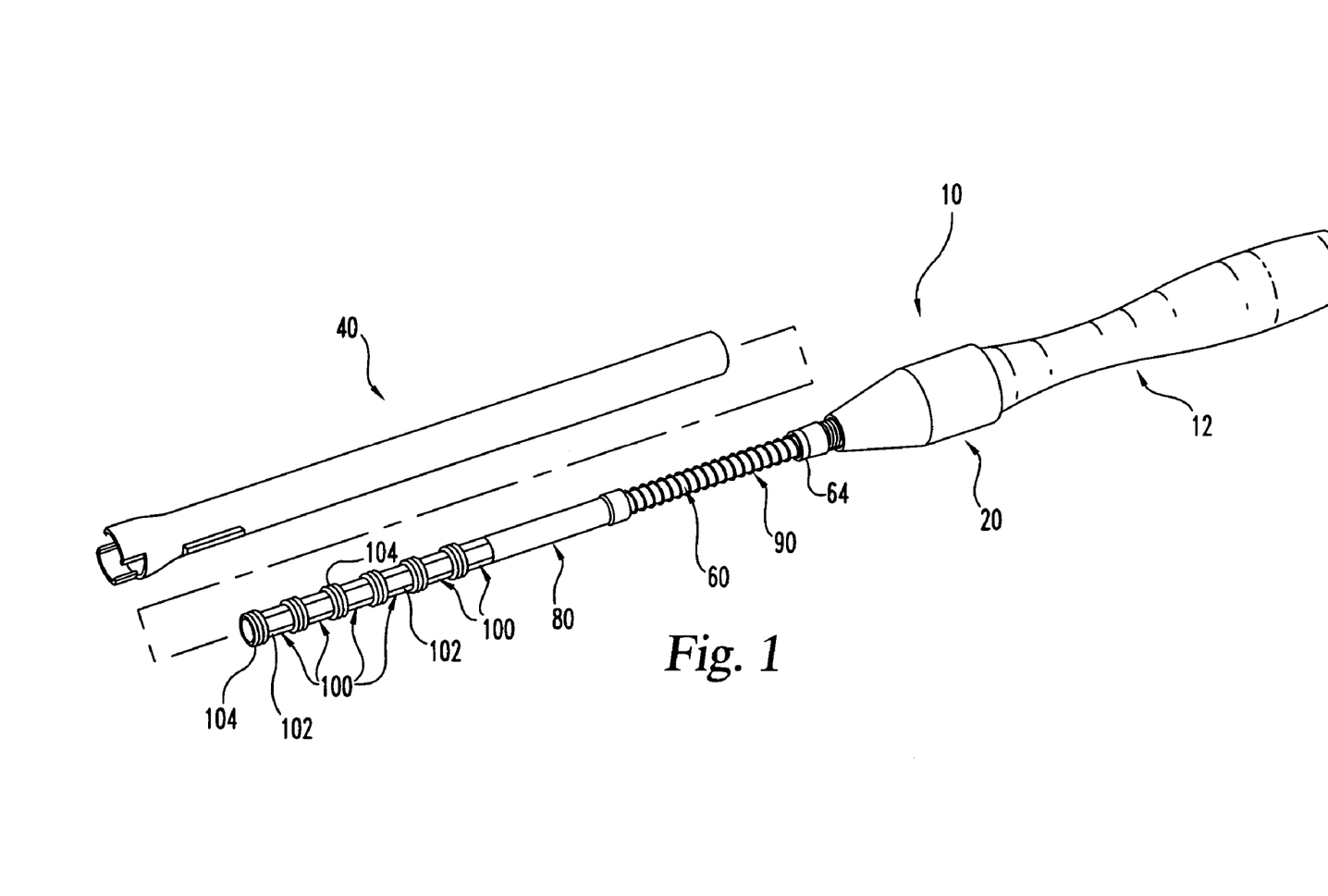
FIG. 1 is a partially exploded perspective view of one embodiment delivery instrument with multiple implants positioned along a drive shaft thereof.
Figure 2:
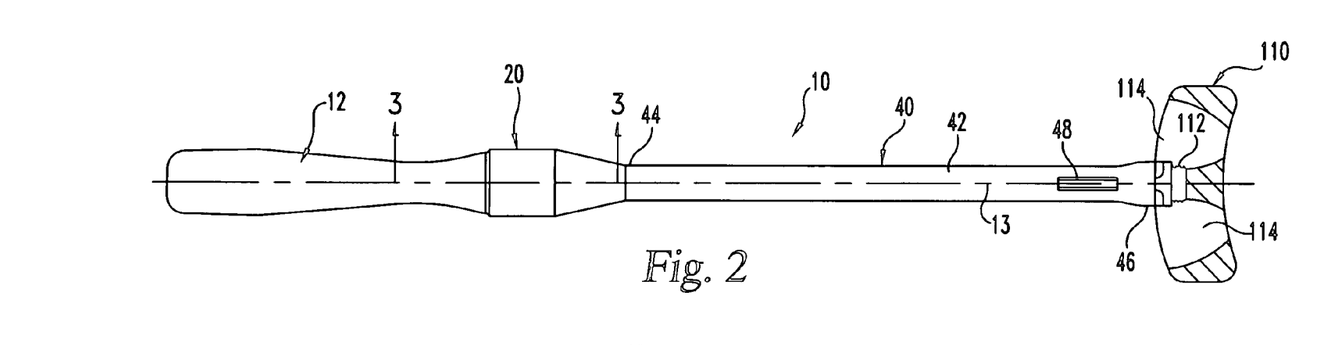
FIG. 2 is an elevation view of the delivery instrument of FIG. 1 positioned adjacent a receiving member.
Figure 3:
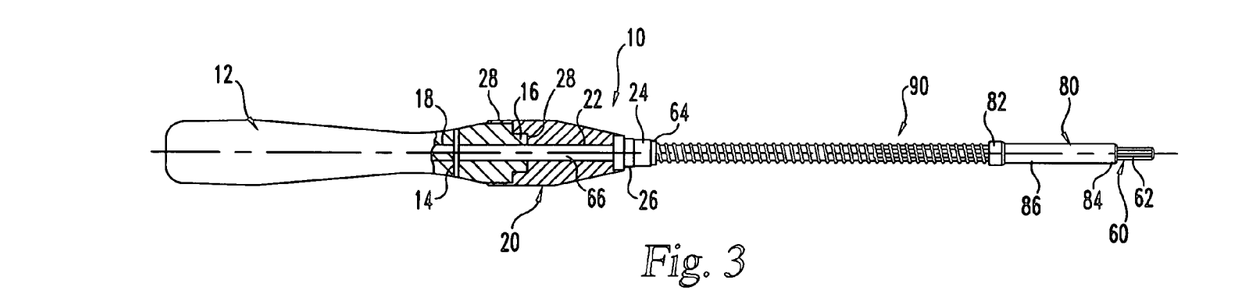
FIG. 3 is a partial section view of the delivery instrument of FIG. 2 with the partial section taken along line 3-3 of FIG. 2.

In FIGS. 1-3 there is shown a delivery instrument 10 extending along a longitudinal axis 13 and including a handle member 12 and a mounting member 20 mounted distally of and rotatable relative to handle member 12. A drive shaft 60 is coupled to handle member 12 and extends distally through mounting member 20. A biasing member 90 is positioned about drive shaft 60, and extends between a collar 64 of drive shaft 60 and a slide member 80. Slide member 80 is slidingly received about drive shaft 60. Biasing member 90 and slide member 80 define an internal passage sized to permit drive shaft 60 to rotate therein. A number of implants 100 are positioned axially along drive shaft 60 distally of slide member 80. Biasing member 90 distally biases slide member 80 along drive shaft 60 into contact with the proximal-most implant 100.

Figure 4:
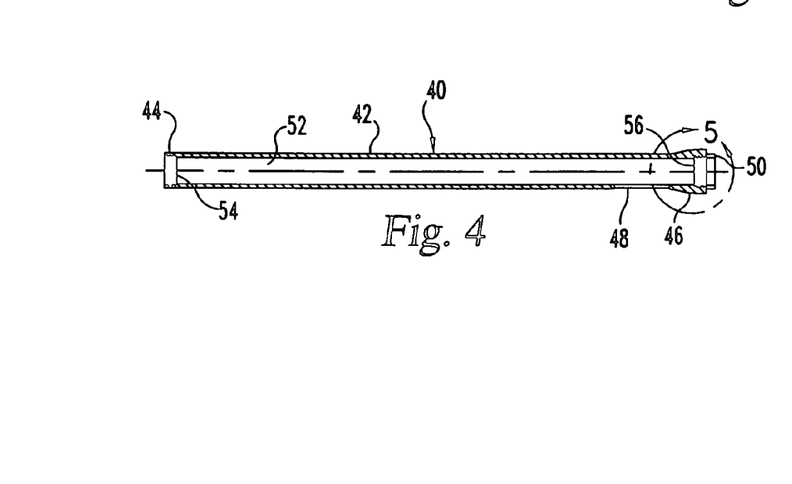
FIG. 4 is a longitudinal section view of the housing member of the delivery instrument of FIG. 2.
Figures 5, 6:
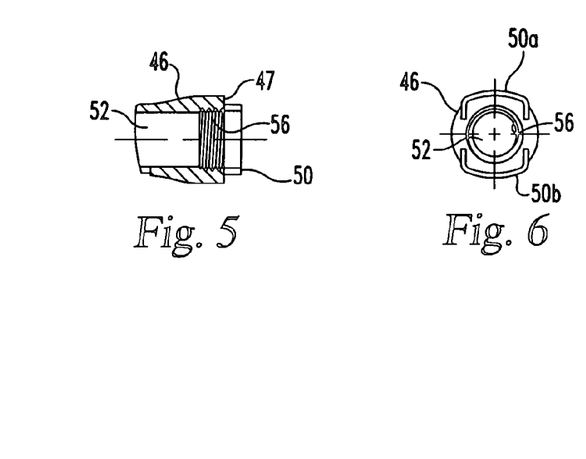
FIG. 5 is an enlarged detailed view of the distal end of the housing member of FIG. 4.
FIG. 6 is a right end elevation view of the housing member of FIG. 4.

Housing member 40 is shown separated from delivery instrument 10 in FIG. 1 and secured to delivery instrument 10 in FIG. 2. As also shown in FIGS. 4-6, housing member 40 includes an internal longitudinal bore 52 so it can be positioned about drive shaft 60, biasing member 90, slide member 80, and implants 100. Proximal end 44 of housing member 40 is engaged to a distal end of mounting member 20. Housing member 40 includes an elongated body 42 extending to a distal end 46 located adjacent to the distal end of drive shaft 60. Implants 100 are delivered to the implantation location through an opening of housing member 40 at distal end 46 by manipulating drive shaft 60 with handle member 12.

Housing member 40 is shown in longitudinal section view in FIG. 4. Housing member 40 includes elongated body 42 defining a central axial bore 52 that extends between and opens at proximal end 44 and distal end 46. Proximal end 44 includes internal threaded portion 44a along a proximal end portion of bore 52, and distal end 46 includes internally thread portion 56 along a distal end portion of bore 52. The external wall of housing member 40 adjacent distal end 46 is flared outwardly to provide an increased wall thickness at distal end wall 47, as shown in FIG. 5.

A flange 50 extends distally from distal end wall 47. In the illustrated embodiment, flange 50 includes first and second portions 50a, 50b located on opposite sides of end wall 47 about bore 52, as shown in FIG. 6. First and second portions 50a, 50b define a generally rectangular shape in the illustrated embodiment. The shape of flange 50 facilitates placement and engagement of delivery instrument 10 in a particular orientation and location with respect to a receiving member 110, such as shown in FIG. 2, and also guides the implants to the implantation location. This can facilitate delivery of a respective one of the implants 100 into the receptacle 112 in a proper or desired orientation. A window 48 is provided adjacent distal end 46 in communication with central bore 52. Window 48 provides for viewing implants 100 in housing member 40 so that it can be readily determined when the last ones of the implants 100 are to be delivered or have been delivered.

Figure 7:
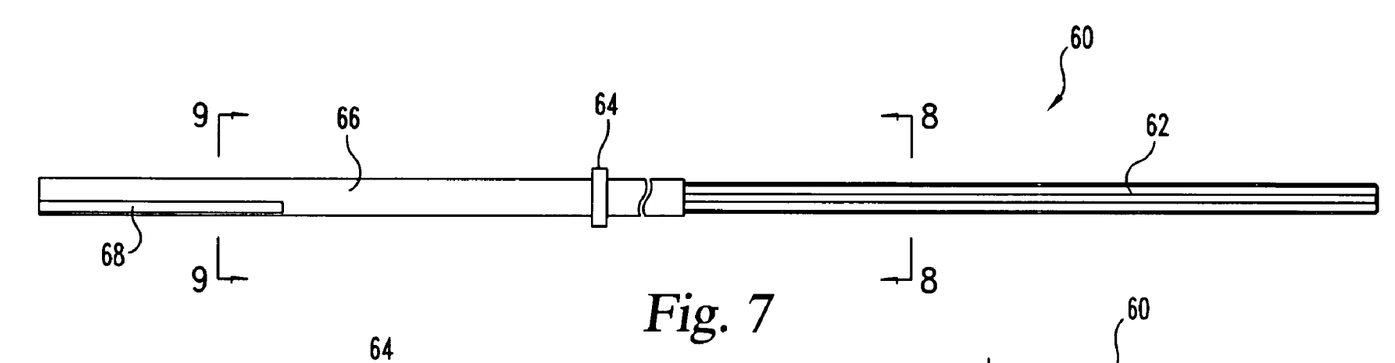
FIG. 7 is an elevation view of a drive shaft of the delivery instrument of FIG. 2.
Figure 8:
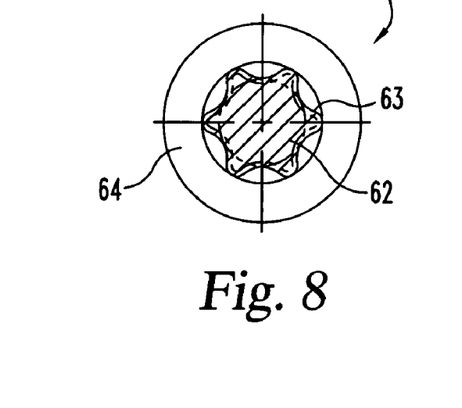
FIG. 8 is an enlarged section view along line 8-8 of FIG. 7.

FIG. 7 shows drive shaft 60. Drive shaft 60 includes a distal implant engaging portion 62, a proximal handle engaging portion 66, and a collar 64 therebetween. Implant engaging portion 62 includes an elongated outer surface portion 63 configured to engage an internal bore of implants 100 to deliver a driving force thereto. In FIG. 8, outer surface 63 includes a non-circular shape to form a TORX type driver arrangement that engages a correspondingly shaped bore extending axially through the implants 100. Other embodiments contemplate other engagement relationships between implants 100 and implant engaging portion 62, including polygonal shapes, non-circular shapes, and ball-detent mechanisms, for example.

Figure 9:
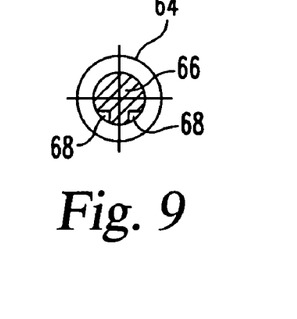
FIG. 9 is a section view along line 9-9 of FIG. 7.

Handle engaging portion 66 includes an elongated cylindrical form that is axially positioned in bore 18 of handle member 12, as shown in FIG. 3. A pin 14 extends through handle member 12 and engaging portion 66 to axially secure drive shaft 60 to handle member 12. Engaging portion 66 further includes axial slots 68 extending therealong in an outer surface thereof as also shown in FIG. 9. Slots 68 receive correspondingly shaped rails (not shown) in bore 18 of handle member 12 to key drive shaft 60 to handle member 12 and prevent drive shaft 60 from rotating relative to handle member 12. As handle member 12 is rotated, drive shaft 60 rotates therewith.

Referring to FIG. 3, mounting member 20 includes a proximally opening receptacle 28 for receiving distal extension 16 of handle member 12. A proximal flange 28 of mounting member 20 extends about handle member 12. Mounting member 20 further includes a central bore 22 through which handle engaging portion 66 of drive shaft 60 extends. Mounting member 20 also includes a distal coupling member 24 having external threads 26. Internal threads 54 of housing member 40 are threadingly engageable with external threads 26 to axially secure housing member 40 with mounting member 20, as shown in FIG. 2.

Collar 64 projects radially outwardly from between portions 62, 66, and is positioned in abutting engagement with a distal end of mounting member 20 at coupling member 24. Collar 64 accordingly axially retains mounting member 20 in engagement with handle member 12, yet allows handle member 12 to rotate relative to mounting member 20 and housing member 40. Housing member 40 is positioned about the implants 100, drive shaft 60 and collar 64, biasing member 90 and slide member 80 and threadingly engaged to coupling member 24 of mounting member 20. The distal end opening of housing member 40 is sized to prevent axial passage of implants 100 therethrough unless implants 100 are threaded through the internally threaded distal portion of bore 52, as discussed further below.

In use, the surgeon or attendant can grasp handle member 12 and mounting member 20, and rotate handle member 12 which in turn rotates drive shaft 60 relative to housing member 40 and mounting member 20. This causes implants 100 to rotate within housing member 40. The distal most implant 100 includes an externally threaded portion 104 (FIG. 1) that threadingly engages the internal threads 56 of housing member 40. Further rotation of handle member 12 causes drive shaft 60 to rotate and advance the distal most implant 100 along threads 56 of housing member 40.

Delivery instrument 10 can be positioned adjacent a receiving member 110, such as shown in FIG. 2, to receive implant 100 when dispensed therefrom. In the illustrated embodiment, receiving member 110 includes an internally threaded receptacle 112 to receive threaded portion 104 of implant 100. As threaded portion 104 exits housing member 40, it comes into contact with receptacle 112 of receiving member 110. Flange 50 can engage receptacle 112 to maintain alignment of delivery instrument 10 therewith, reducing any potential for cross-threading of implant 100 in receptacle 112. Drive shaft 60 maintains engagement with implant 100 in head portion 102 as threaded portion 104 is distally advanced from the distal end of drive shaft 60. Further rotation of drive shaft 60 with handle member 12 rotates implant 100 and threadingly engages it to receptacle 112 of receiving member 110. When implant 100 is seated in receiving member 110, proximal head portion 102 of implant 100 can be configured to sever or break-off from threaded portion 104 when sufficient torque is applied thereto with drive shaft 60.

As the distal-most implant 100 is secured in receptacle 112, the second most-distal implant 100 advances distally along drive shaft 60 until its threaded portion 104 engages internal threads 56 of housing member 40. When the distal-most implant 100 is dispensed from delivery instrument 10, the threaded portion 104 of the next most-distal implant 100 is threadingly engaged with threaded portion 56, which retains the implant in delivery instrument 10 while the first implant is being engaged to the first receptacle. Delivery instrument 10 can be relocated to a second receptacle of receiving member 110, or to a receptacle of another receiving member, for securement of a second implant 100 thereto. The process can be repeated until the desired number of implants have been delivered, or until all implants have been delivered from delivery instrument 10.

Additional implants 100 can be conveniently re-loaded by removing housing member 40 and placing additional implants 100 therein through the opening to bore 52 at proximal end 44. Drive shaft 60 can then be aligned with the aligned central bores of the implants 100 in housing member 40, and inserted therethrough from proximal end 44. When a distal end 84 of slide member 80 contacts the implants 100, biasing member 90 compresses and slide member 80 slides proximally along drive shaft 60 until housing member 40 can be engaged to coupling member 24. In the illustrated embodiment, biasing member 90 is a coil spring engaged to a proximal collar 82 of slide member 80, and has a length in a relaxed state that maintains a body 86 of slide member 80 along drive shaft 60, as shown in FIG. 3. Accordingly, slide member 80 does not fall off the end of drive shaft 60 when housing member 40 is removed, and a distal portion of drive shaft 60 remains exposed to facilitate positioning of it into the implants 100.

Other embodiments contemplate that instrument 10 does not include slide member 80 and/or biasing member 90. Rather, biasing member 90 can directly contact the implants, or the implants can simply self-feed toward the distal end of housing member 40 by gravity as the distal most implant is delivered therefrom.

Another embodiment delivery instrument contemplates that implants 100 are not retained on drive shaft 60 by the internal threads of housing member 40. Rather, a c-clip or O-ring on drive shaft 60 interferes with and retains implants 100 thereon until sufficient force is applied to advance implants 100 distally along the drive shaft 60 for delivery to the implantation location. In yet another form, the implants can be retained on drive shaft 60 by frictional engagement with drive shaft 60.

Figure 10:
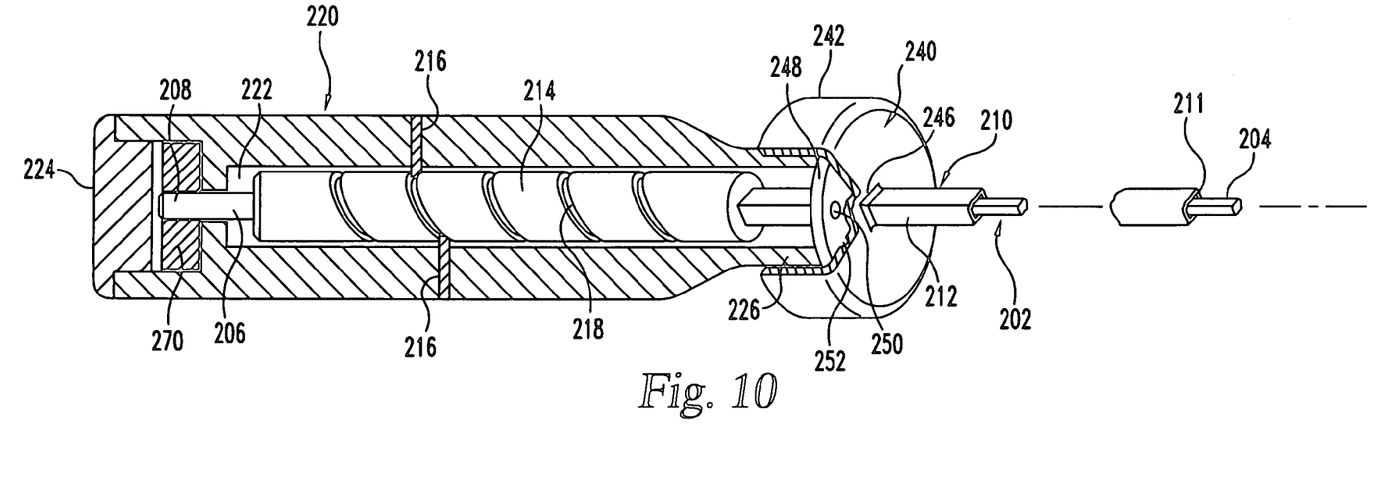
FIG. 10 is a view in partial section of a proximal portion of another embodiment delivery instrument.

Another embodiment delivery instrument 200 is shown in FIG. 10. In FIG. 10 the distal end of the delivery instrument 200 is not shown, it being understood that delivery instrument 200 includes a drive shaft 202 with a distal implant engaging portion 204 that can be configured similarly to implant engaging portion 62 of drive shaft 60. Drive shaft 202 can be located within a slide member 210 that is manually movable to displace implants distally along implant engaging portion 204. Drive shaft 202 includes a proximal portion 206 extending through slide member 210 to a proximal end 208 in handle member 220. Proximal portion 206 can be secured to handle member 220.

Handle member 220 defines a central bore 222 and includes an end cap 224 at the proximal end thereof. Bore 222 opens distally at a distal end 226 of handle member 220. The distal end 226 includes a mounting member 240 positioned therearound that is rotatable relative to handle member 220. Mounting member 240 can be retained on handle member 220 with a snap ring or other suitable connection device with an external wall 242 extending proximally along a distal portion of handle member 220 to provide a surface area to grasp mounting member 240. Mounting member 240 further includes a distal bore 246 keyed with a non-circular region 212 of slide member 210 so that rotation of mounting member 240 rotates slide member 210 about drive shaft 202 and within handle member 220.

A rotation plate 248 can be situated between the distal end 226 of handle member 220 and mounting member 240. One or more ball plunger devices 250 (only one shown) can be situated between rotation plate 248 and mounting member 240 on opposite sides of slide member 210. The ball plunger devices 250 can reside in detents 252 in one of mounting member 240 and rotation plate 248 at certain rotational positions of mounting member 240 about handle member 220.

Slide member 210 further includes a proximal grooved or threaded region 214 within handle member 220. Threaded region 214 includes an outer thread profile 218. Travel pins 216 are engaged to handle member 220 and extend from opposite sides of handle member 220 to reside in thread profile 218. Travel pins 216 axially advance or retract slide member 210 along drive shaft 202 as slide member 210 is rotated in handle member 220 by rotation of mounting member 240.

In use, the distal-most implant on the distal end of drive shaft 202 can be engaged to a receiving member by rotating the entire delivery instrument 200 with handle member 220. After the distal-most implant is engaged to the receiving member, the next most distal implant can be axially advanced along drive shaft 202 for engagement with a second receptacle in the receiving member or with a second receiving member. The user grasps mounting member 240 and rotates mounting member 240 relative to handle member 220, in turn rotating slide member 210 in handle member 220 and about drive shaft 202. Rotation of slide member 210 moves travel pins 216 along thread profile 218, which in turn causes distal and axial displacement of slide member 210 about drive member 202 so that its distal end 211 distally displaces the implants positioned about drive member 202.

Thread profile 218 can be provided with a pitch so that the ball plungers 250 move from one detent to the next adjacent detent in response to a pre-determined distance of axial advancement of slide member 210 along drive shaft 202. In one form, this pre-determined distance corresponds to the length of an implant along drive shaft 202. When the distal-most implant is delivered, an incremental advancement of slide member 210 with rotation of mounting member 240 advances the next implant distally to a location adjacent the distal end of drive shaft 202 for delivery to the next implant receptacle. Various forms for position indicators are contemplated, including dials and ball-detent mechanisms extending between the mounting member and the handle member, for example, that can provide an audible click and/or slight resistance to rotation of the mounting member relative to the handle member when an incremental rotation has been attained therebetween.

In one embodiment, delivery instrument 200 can include a torque limiting device 270 that couples drive shaft 202 to handle member 220. Torque limiting device 270 can be structured to prevent excessive torque from being applied to the implant by causing drive shaft 202 to slip relative to handle member 220 when a threshold torque is applied to the implant with the drive shaft. In yet another embodiment, a torque indicator can provide an indication of the applied torque to the implant. In either embodiment, the implants can include a proximal break-off portion that severs relative to the distal threaded portion upon application of a threshold torque thereto. Still other embodiments contemplate that the implant only includes a threaded portion for engaging the receiving member without any proximal break-off portion or any head portion.

Receiving member 110 can be an implant engageable to bony structure of the patient, such as a spinal plate, a bone screw, a clamp, an interbody device, or any other construct structured to receive an implant. For example, in FIG. 2 receiving member 110 includes holes 114 to receive bone screws to secure it to the bony structure. Implant 100 is positioned in receptacle 112 in overlapping relation to at least one of the holes 114 to prevent the screws from backing out thereof. In another example, the receiving member is a proximal portion of a screw and is configured to receive a spinal rod or other elongated connecting element therein, and the implants secure the spinal rod or elongated connecting element in the receiving member. In another specific application, the implant is engaged to one or more bony elements of the spinal column. In another embodiment, implant 100 is structured for engagement directly to bony or soft tissue of the patient.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical system, comprising:
a receiving member implantable in a patient, said receiving member including at least one receptacle;
an instrument including a handle member, a drive shaft engaged with and extending distally from said handle member along a longitudinal axis, said drive shaft being rotatable with said handle member, and a housing member coupled with said handle member and extending longitudinally about said drive shaft, said handle member being rotatable relative to said housing member and further comprising a compressible biasing member and a slide member positioned about said drive shaft; and
a plurality of implants positioned along said drive shaft, wherein said drive shaft extends through said plurality of implants and said plurality of implants are movable along said drive shaft toward a distal end of said drive shaft, at least one of said implants being engageable in said receptacle of said receiving member when delivered from a distal end of said drive shaft through a distal end opening of said housing member as said handle member and said drive shaft are rotated relative to said housing member.

2. The system of claim 1, wherein said receiving member is engageable to a spinal column of the patient and said implants are externally threaded set screws threadingly engageable in said at least one receptacle.

3. The system of claim 2, wherein each of said externally threaded set screws includes a frangible head portion.

4. The system of claim 1, further comprising a mounting member coupled between a distal end of said handle member and a proximal end of said housing member, wherein said handle member and said drive shaft are rotatable relative to said mounting member.

5. The system of claim 4, wherein said drive shaft includes a collar extending radially outwardly therefrom and said distal end of said mounting member abuttingly engages said collar.

6. The system of claim 5, wherein said drive shaft includes an implant engaging portion extending distally from said collar and a handle engaging portion extending proximally from said collar, said handle engaging portion extending through said mounting member and being coupled with said handle member.

7. The system of claim 1, wherein said housing member includes a flange extending distally from a distal end wall of said housing member, said flange being positionable in contact with said receiving member adjacent said receptacle.

8. The system of claim 1, wherein said housing member includes a window adjacent to said distal end opening and in communication with an internal bore defined by said housing member.

9. The system of claim 1, wherein said plurality of implants is positioned distally of said slide member and said biasing member distally biases said slide member into contact with a proximal most one of said plurality of implants.

10. A surgical system, comprising:
a receiving member implantable in a patient, said receiving member including at least one receptacle;
an instrument including a handle member, a drive shaft engaged with and extending distally from said handle member along a longitudinal axis, said drive shaft being rotatable with said handle member, and a housing member coupled with said handle member and extending longitudinally about said drive shaft, said handle member being rotatable relative to said housing member; and
a plurality of implants positioned along said drive shaft, wherein said drive shaft extends through said plurality of implants and said plurality of implants are movable along said drive shaft toward a distal end of said drive shaft, at least one of said implants being engageable in said receptacle of said receiving member when delivered from a distal end of said drive shaft through a distal end opening of said housing member as said handle member and said drive shaft are rotated relative to said housing member, wherein said receiving member is engageable to a spinal column of the patient and said implants are externally threaded set screws threadingly engageable in said at least one receptacle and said housing member includes an internally threaded portion adjacent said distal end opening, said set screws threadingly passing through said internally threaded portion of said housing member for delivery from said distal end of said drive shaft.

11. The system of claim 10, wherein said housing member is externally flared adjacent to said internally threaded portion.

12. A surgical system, comprising:
a receiving member implantable in a patient, said receiving member including at least one receptacle;
an instrument including a handle member, a drive shaft engaged with and extending distally from said handle member along a longitudinal axis, said drive shaft being rotatable with said handle member, and a housing member coupled with said handle member and extending longitudinally about said drive shaft, said handle member being rotatable relative to said housing member; and
a plurality of implants positioned along said drive shaft and movable therealong toward a distal end of said drive shaft, at least one of said implants being engageable in said receptacle of said receiving member when delivered from a distal end of said drive shaft through a distal end opening of said housing member as said handle member and said drive shaft are rotated relative to said housing member;
a mounting member coupled between a distal end of said handle member and a proximal end of said housing member, wherein said handle member and said drive shaft are rotatable relative to said mounting member;
wherein said drive shaft includes a collar extending radially outwardly therefrom and said distal end of said mounting member abuttingly engages said collar;
wherein said drive shaft includes an implant engaging portion extending distally from said collar, wherein said implant engaging portion of said drive shaft is positioned through said plurality of implants and said plurality of implants are movable along said implant engaging portion toward said distal end of said drive shaft, said drive shaft including a handle engaging portion extending proximally from said collar, said handle engaging portion extending through said mounting member and being coupled with said handle member; and
further comprising a compressible biasing member extending distally from said collar to a slide member slidingly received about said implant engaging portion of said drive shaft, said slide member contacting a proximal-most one of said plurality of implants, said biasing member and said slide member biasing said plurality of implants distally along said drive shaft and wherein rotation of said handle member rotates said implant engaging portion of said drive shaft and further rotates said plurality of implants through which said implant engaging portion extends.

13. A surgical system, comprising:
an instrument including a handle member, a drive shaft engaged with and extending distally from said handle member along a longitudinal axis, a housing member coupled with said handle member and extending longitudinally about said drive shaft, wherein said drive shaft is rotatable relative to said housing member with said handle member and said housing member includes an internally threaded portion adjacent a distal end opening thereof; and
a plurality of implants positioned in said housing member along and about said drive shaft and movable therealong toward a distal end of said drive shaft, wherein said drive shaft extends through said plurality of implants so that rotation of said drive shaft with said handle rotates said plurality of implants in said housing and said plurality of implants including an externally threaded portion engageable to said internally threaded portion of said housing member when aligned therewith as respective ones of said implants are threadingly advanced through said housing by rotation of said drive shaft with said handle member.

14. The system of claim 13, further comprising a receiving member implantable in a patient, said receiving member including at least one threaded receptacle for receiving at least one of said plurality of implants therein.

15. The system of claim 13, wherein said housing member includes a window adjacent to said distal end opening and in communication with an internal bore defined by said housing member.

16. The system of claim 13, further comprising a compressible biasing member and a slide member positioned about said drive shaft.

17. The system of claim 16, wherein said plurality of implants is positioned distally of said slide member and said biasing member distally biases said slide member into contact with a proximal most one of said plurality of implants.

18. The system of claim 13, wherein said housing member is externally flared adjacent to said internally threaded portion.

\* \* \* \* \*